(12) United States Patent
Ishiguro et al.

(10) Patent No.: US 9,251,992 B2
(45) Date of Patent: Feb. 2, 2016

(54) STEREO X-RAY GENERATING DEVICE

(75) Inventors: Yoshihisa Ishiguro, Tokyo (JP); Masanori Haba, Tokyo (JP)

(73) Assignee: MICRO-X JAPAN LTD., Tokyo (JP)

( * ) Notice: Subject to any disclaimer, the term of this patent is extended or adjusted under 35 U.S.C. 154(b) by 175 days.

(21) Appl. No.: 14/236,562

(22) PCT Filed: Jul. 27, 2012

(86) PCT No.: PCT/JP2012/069186
§ 371 (c)(1),
(2), (4) Date: May 14, 2014

(87) PCT Pub. No.: WO2013/018712
PCT Pub. Date: Feb. 7, 2013

(65) Prior Publication Data
US 2014/0376698 A1 Dec. 25, 2014

(30) Foreign Application Priority Data

Aug. 2, 2011 (JP) ................................. 2011-169258

(51) Int. Cl.
| | |
|---|---|
| *A61B 6/02* | (2006.01) |
| *H01J 35/06* | (2006.01) |
| *G01N 23/04* | (2006.01) |

(Continued)

(52) U.S. Cl.
CPC ................. *H01J 35/06* (2013.01); *A61B 6/022* (2013.01); *A61B 6/4028* (2013.01); *G01N 23/043* (2013.01); *H01J 35/08* (2013.01); *H01J 35/16* (2013.01); *H01J 35/26* (2013.01); *A61B 6/06* (2013.01); *G01N 2223/204* (2013.01); *G01N 2223/414* (2013.01); *H01J 35/10* (2013.01);

(Continued)

(58) Field of Classification Search
CPC ........ A61B 6/022; A61B 6/06; A61B 6/4028; G01N 2223/204; G01N 2223/414; G01N 23/043

See application file for complete search history.

(56) References Cited

U.S. PATENT DOCUMENTS

| | | | |
|---|---|---|---|
| 4,712,226 A | 12/1987 | Horbaschek | |
| 5,469,429 A * | 11/1995 | Yamazaki | H01J 35/24 378/113 |

(Continued)

FOREIGN PATENT DOCUMENTS

| | | | | |
|---|---|---|---|---|
| DE | 712816 C | * | 10/1941 | ............. H01J 35/26 |
| DE | 875975 C | * | 5/1953 | ............. H01J 35/26 |

(Continued)

OTHER PUBLICATIONS

International Search Report prepared by the Japanese Patent Office on Oct. 2, 2012, for International Application No. PCT/JP2012/069186.

*Primary Examiner* — David J Makiya
*Assistant Examiner* — John Corbett
(74) *Attorney, Agent, or Firm* — Sheridan Ross P.C.

(57) ABSTRACT

The purpose of the present invention is to provide a stereo x-ray radiation device that is small and for which handling is simple. One cathode that functions as an emitter and two anodes that function as targets are disposed in a single straight-tube shaped vacuum vessel. The stereo x-ray generating device is characterized by the cathode being a cold cathode disposed in the center part of the vessel, the anodes being disposed each to one end of the vessel, and the spaces between the anodes disposed in the two ends of the vessel and the cathode being constituted such that the same can be moved closer or apart along the axial line of the vessel.

10 Claims, 3 Drawing Sheets

(51) Int. Cl.
*H01J 35/26* (2006.01)
*A61B 6/00* (2006.01)
*H01J 35/08* (2006.01)
*H01J 35/16* (2006.01)
*H01J 35/10* (2006.01)
*A61B 6/06* (2006.01)

(52) U.S. Cl.
CPC ...... *H01J 2235/062* (2013.01); *H01J 2235/086* (2013.01)

(56) References Cited

U.S. PATENT DOCUMENTS

| | | | |
|---|---|---|---|
| 6,125,167 A * | 9/2000 | Morgan | H01J 35/10 378/121 |
| 2010/0002829 A1 * | 1/2010 | Dafni | A61B 6/032 378/9 |
| 2010/0080357 A1 * | 4/2010 | Katcha | H01J 35/10 378/124 |

FOREIGN PATENT DOCUMENTS

| | | | | |
|---|---|---|---|---|
| DE | 1236821 B | * | 3/1967 | A61B 6/022 |
| DE | 102010061992 A1 | * | 5/2012 | A61B 6/022 |
| DE | 102011087705 B3 | * | 3/2013 | H01J 35/10 |
| JP | 53097387 A | * | 8/1978 | |
| JP | H09-187447 | | 7/1997 | |
| JP | 2007-280958 | | 10/2007 | |
| JP | 2010-186694 | | 8/2010 | |

* cited by examiner (A)

(B)

STEREO X-RAY GENERATING DEVICE

CROSS REFERENCE TO RELATED APPLICATIONS

This application is a national stage application under 35 U.S.C. 371 and claims the benefit of PCT Application No. PCT/JP2012/069186 having an international filing date of Jul. 27, 2012, which designated the United States, which PCT application claimed the benefit of Japanese Application No. 2011-169258 filed Aug. 2, 2011, the disclosure of both the above-identified applications are incorporated herein by reference.

FIELD OF THE INVENTION

This invention relates to a x-ray generating device which aims an electron beam to hit a target and generates an x-ray. In particular, it relates to an x-ray generating device which has two anodes (target) corresponding to one cathode (emitter).

BACKGROUND ART

X-ray generating devices are incorporated in non-destructive inspection equipment.

Regarding the structure of the x-ray generating device, an electronic source (emitter), a target and a grid electrode (middle electrode) are arranged in one glass tube. To generate an electron, a voltage is applied between the electronic source and the grid electrode and the generated electron is made to hit the target by applying a voltage between the grid electrode and the target.

In addition to the X-ray generating device of a 3 electrode structure, an x-ray generating device to photograph a stereo image is disclosed in Patent Document 1.

To capture the three-dimensional image of the subject, the device disclosed in Patent Document 1 provides an x-ray tube for the left hand image and an x-ray tube for the right hand image.

The subject is irradiated from each x-ray tube alternatively, the observer views a transparent image provided by one x-ray tube with the right eye, and views a transparent image provided by the other x-ray tube with the left eye.

In Patent Document 1, to change the photography amplification of the transparent image, the distance of the pair of x-ray tubes can be varied. A rack and pinion mechanism and a ball-thread mechanism are exemplified as the variable mechanism.

Patent document 2 discloses a structure such that a plurality of cathode and a discal anode are provided in one vacuum tube. The purpose of Patent document 2 is not to gain a three-dimensional image.

The anode is comprised of a plurality of segments, x-rays with different strengths are given out from every segment by hitting the turning anodal segment with the electron beam emitted from the cathode.

PATENT DOCUMENT

[Patent Document 1] Japanese Laid Open Patent Hei09-187447

[Patent Document 2] U.S. Pat. No. 4,712,226

DISCLOSURE OF THE INVENTION

Problems Solved by the Invention

When photographing a three-dimensional image enlargement, the image detail becomes unclear and the picture quality is reduced by having merely enlarged the photographed image.

To gain a high quality enlarged image, it is necessary to change the distance between the x-ray tube and the subject and the distance between the x-ray tube and the x-ray detector.

Herein, to gain a three-dimensional image (stereo image), an x-ray tube for the left-hand image and an x-ray tube for the right-hand image are required.

It is necessary to change the distance of the x-ray tubes of right-hand and left-hand side, because the edge part of the subject will be located in the unstable end of the x-ray radiation area. This can only be done by changing the distance between the x-ray tube and the subject or changing the distance between the x-ray tube and the x-ray detector.

The stereo x-ray tube device disclosed in Patent Document 1 requires two x-ray tubes to be provided, therefore, the overall system size is increased, and the number of parts will also increase.

To photograph an enlarged image, the stereo x-ray tube device disclosed in Patent Document 1 arranges two x-ray tubes in parallel. The position of the two x-ray sources (focus) is made variable by making the two x-ray tubes come close to or move away from each other using a rack and pinion mechanism or a ball-thread mechanism.

In an examination, the position of the subject (patient) may shift or its organic form may change in one breathing, accordingly, it is preferable to carry out the photography of the normal magnification and the enlarged image in one heartbeat.

However, because the device disclosed in Patent Document 1 uses a rack and pinion mechanism or a ball-thread mechanism, the response speed of the device disclosed in Patent Document 1 becomes slow due to the time required for adjustment.

On the other hand, in the x-ray generating device which is disclosed in patent document 2, the turning anode is comprised of a plurality of segments, and it is substantially equal to a plurality of anodes being arranged in one tube.

However, because the cathode is arranged in response to each segment, then a plurality of cathodes are arranged too.

Also, Patent Document 2 does not disclose an assumption that the distance between two anodes is at all variable.

Means For Solving the Problems

To solve the above described problem, the stereo x-ray generating device of the present invention is characterized;

One cathode which functions as an emitter and two anodes which function as targets are disposed in a straight tubular vacuum chamber, the cathode is a cold cathode and is disposed in the central part of the chamber, the anodes are disposed at each end of the chamber, the length of the spaces between the anodes disposed at each end of the chamber and the cathode can be expanded or reduced along the axis of the chamber.

Moving the anodes closer together or apart along the axis is not limited to one method only. For example, it is expected that electrification to an electromagnet, electrification to a solenoid, or alternatively rotation of the anode may be used.

When a conventional heat filament is adopted as a cathode, due to the electronic generation by the electrification, stabilization requires time and the quantity of electronic generation cannot to be changed instantly.

Thus, in the present invention, a cold cathode is used. The cold cathode does not need an external application of heat energy for electronic release.

As for this cold cathode, a structure formed from carbon film, such as a carbon nano-tube, graphen carbon nano wall or special shape nano carbon structure on the electron emission surface is preferable.

Effect of the Invention

According to the stereo x-ray generating device of the present invention, using one x-ray generation tube, x-rays can be generated from two spaced-apart places. Also, the distance between the x-ray sources can be changed.

Particularly, because the distance of the x-ray sources can be changed in a flash/second, it is superior in the photography and enlargement of a three-dimensional image of the subject (patient).

BEST MODE FOR CARRYING OUT THE INVENTION

An embodiment of the present invention is explained below based on the attached drawing.

Figure 1:
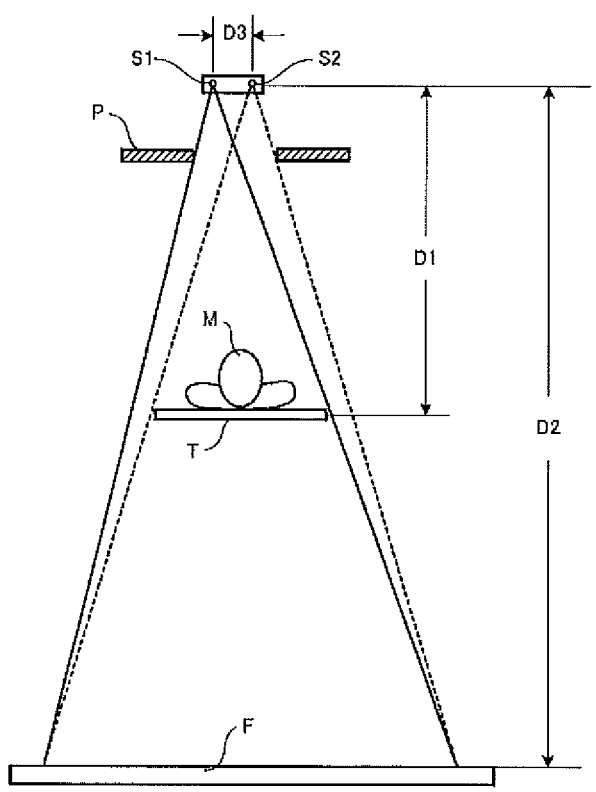
FIG. 1 General view of an imaging device which applied the stereo x-ray generating device of the present invention.

FIG. 1 is a general view of an imaging device which applied the stereo x-ray generating device of the present invention, A stereo x-ray generating device 1 of the present invention is positioned in the upside of a table T on which is placed a subject M, an x-ray detector F detecting x-rays which are transmitted is arranged below the table T.

Also, the stereo x-ray generating device 1 comprises two x-ray sources S1, S2 spaced in right and left, a diaphragm board P is arranged directly under the stereo x-ray generating device 1, the diaphragm board P limits the x-ray irradiation width generated from the x-ray sources S1, S2.

The x-ray source S1 is the x-ray source for the right side image, the x-ray source S2 is the x-ray source for the left side image, and a three-dimensional image is observed by viewing the right side image with the right eye and the left side image with the left eye simultaneously.

The above described three-dimensional image is enlarged by changing the distance D1 of the stereo x-ray generating device 1 and the subject M, or the distance D2 of the stereo x-ray generating device 1 and the x-ray detector F.

Herein, when it enlarges at magnification, the subject M may be off from the x-radiation width or may cross the outer end of the x-radiation area.

To prevent the above, change the distance D3 between the x-ray sources S1 and S2 in accordance with modification of the distance D1 or D2.

Figure 2:
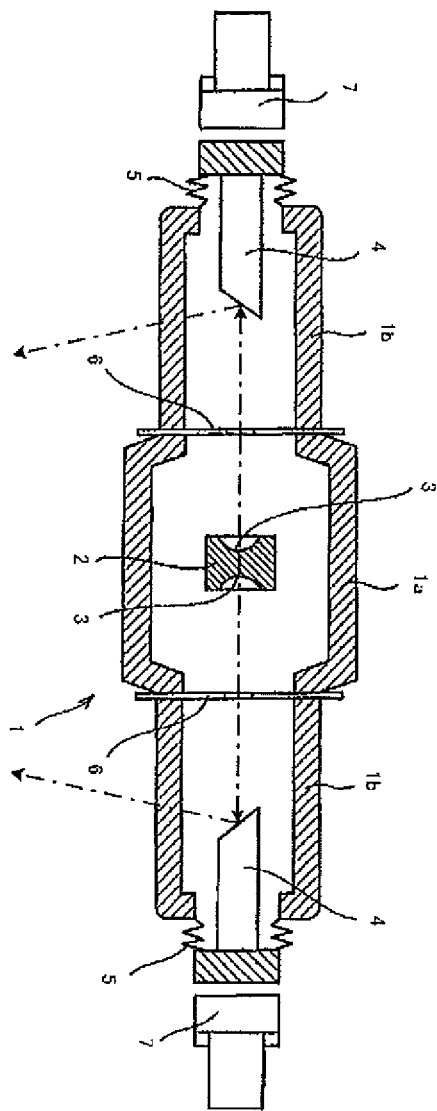
FIG. 2 Sectional view of the stereo x-ray generating device of the present invention.

The stereo x-ray generating device 1 of the present invention in which the distance D3 between the x-ray source S1 and S2 is changeable is explained below based on FIG. 2.

The main body of stereo x-ray generating device 1 is comprised of insulating materials such as ceramic or glass, the shape is a straight tube, and the inside is in a vacuum state.

The central part of the main body of stereo x-ray generating device 1 has a large diameter portion 1a, a cathode 2 is arranged in the large diameter portion 1a, the cathode 2 is comprised of a block-shaped metal base, recesses 3 are formed to both sides of the block-shaped metal base, the surface of the recess 3 becomes an electron emission surface by forming a carbon film on it, the carbon film is for example, carbon nano-tube, graphen, carbon nano wall or a special shaped nano carbon structure, and these carbon films are formed by CVD.

Also, both ends of the main body are a small diameter portion 1b, an anode 4 comprising tungsten or molybdenum is disposed in the small diameter portion 1b, the tip of the anode 4 has an inclined surface where an electron beam collides, the end of anode 4 protrudes outward from the aperture formed on the tube 1 (small diameter portion 1b), a bellows 5 is provided between the end of anode and the aperture, as a result, a vacuum state in tube 1 is maintained, and the anode 4 can move along the axial direction, the distal surfaces of the anode 4 is equivalent to the x-ray source S1, S2.

Also, a middle electrode 6 (ground electrode) is provided in the part where the large diameter portion 1a meets the small diameter portions 1b of the tube 1.

An electron is released from the cathode 2 by applying a voltage between the cathode 2 and the middle electrode 6.

In addition, a released electron converges with the aperture of the ground electrode, by applying a voltage between the middle electrode 6 and the anode 4.

The electron accelerates and collides with the anode 4 (target), and an x-ray is generated.

An electromagnet 7 is arranged outward of the end of the anode 4, the electromagnet 7 is attached to the tip of the insulator.

As a result, when an electric current is sent to the electromagnet 7, the end of the anode 4 is adsorbed to the magnet in a micro-second.

Figure 3:
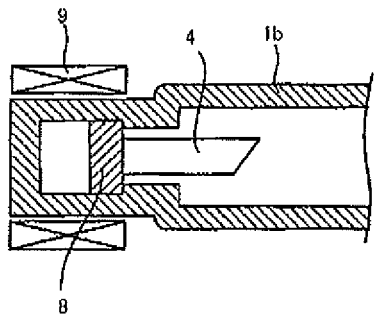
FIG. 3 A figure showing the essential part of the stereo x-ray generating device of the other embodiment.

That is, the right side anode 4 and the left side anode 4 move outward in the axial direction, then the distance D3 between the x-ray source S1 and x-ray source S2 will expand in a micro-second In the other embodiment shown in FIG. 3, a magnetic body 8 is attached to the rearward end of anode 4 in substitution for an electromagnet, and a solenoid 9 is arranged outside of the both ends of the main body, by sending an electric current to the solenoid 9, the anode 4 moves back and forth along the axial direction.

Figure 4:
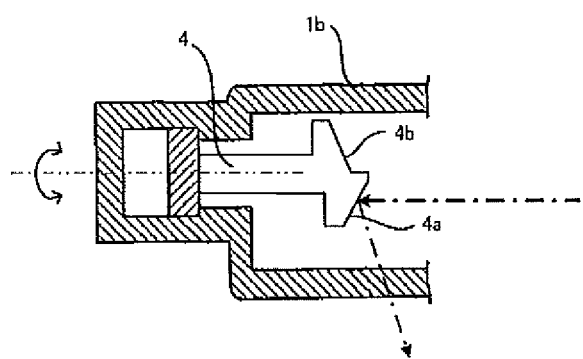
FIG. 4 A figure showing the essential part of the stereo x-ray generating device of the other embodiment.
Figure 4:
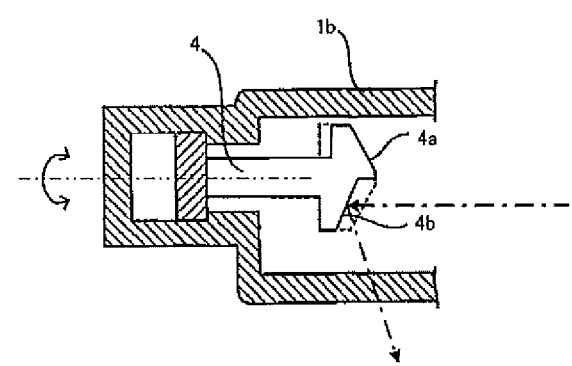

In the other embodiment shown in FIG. 4, a novel adjustment is put on the tip shape of the anode 4, then, the distance between the anode 4 of right and left (distance D3 between the x-ray source S1 and S2) is variable without making the anode 4 move back and forth.

That is, a first inclined surface 4a and a second inclined surface 4b are formed on the tip of the anode 4, the angle of inclination of the first and second inclined surface 4a, 4b are the same, but the axial position and phase are different. The first inclined surface 4a is replaced with the second inclined surface 4b by turning the anode 4 180 degrees around the axis, thus the distance D3 between the x-ray sources is changed.

The above explanation shows one embodiment of the invention.

In addition to the above the means to move the anode back and forward or turn it is arbitrary.

The shape of the main body of stereo x-ray generating device 1 is arbitrary too, for example, it is conceivable to assume in favor of assembling by dividing the tube into 2 or 3 division.

INDUSTRIAL APPLICABILITY

The x-ray generating device of the present invention can be used as a portable Non-Destructive Inspection equipment, or as an x-ray generating device for portable fluorescence x-ray.

EXPLANATIONS OF THE LETTERS AND NUMERALS

1 . . . main body of stereo x-ray generating device,
1*a* . . . large diameter portion,
1*b* . . . small diameter portion,
2 . . . cathode,
3 . . . recess,
4 . . . anode,
4*a* . . . first inclined surface,
4*b* . . . second inclined surface.
5 . . . bellows,
6 . . . middle electrodes,
7 . . . electromagnets,
8 . . . magnetic bodies,
9 . . . solenoids.

The invention claimed is:

1. A stereo x-ray generating device comprising:
   one cathode which functions as an emitter and two anodes which function as targets are disposed in a straight tubular vacuum chamber,
   the cathode is a cold cathode and is disposed in the central part of the chamber,
   the anodes are disposed at each end of the chamber,
   the cathode emits electrons which hit the two targets generating x-rays,
   the space between the two anodes is made variable by expanding or reducing the distance between the anodes along the axis of the chamber by movement of the anodes.

2. The stereo x-ray generating device according to claim 1, with middle electrodes functioning as a grid electrode arranged between the cathode and each anode.

3. The stereo x-ray generating device according to claim 1, the cathode is comprised of:
   a block-shaped metal base,
   recesses formed to both sides of the block-shaped metal base, and
   the surface of the recess becomes an electron emission surface comprising a carbon film.

4. The stereo x-ray generating device according to claim 3, wherein the carbon film is carbon nano-tube, graphene, carbon nano wall or a shaped nano carbon structure.

5. The stereo x-ray generating device according to claim 3, in which the tip of the anode has an inclined surface.

6. The stereo x-ray generating device according to claim 5, in which:
   a magnetic body is attached to the opposite side of each tip of the anode, and
   the movement to and fro of each anode along the axis of the chamber is performed by electrification to the electromagnet or solenoid provided at the end of the chamber.

7. The stereo x-ray generating device according to claim 5, in which:
   a magnetic body is attached to the opposite side of each tip of the anode,
   the movement to and fro of each anode along the axis of the chamber is performed by electrification to the electromagnet or solenoid provided at the end of the chamber,
   the inclined surface consists in two inclined surfaces,
   these two inclined surfaces are provided together on either side of the axis,
   the angle of inclination of the two inclined surfaces are the same,
   the axial positions of the two inclined surfaces are different, and
   the anode and the cathode are moved closer or apart by turning the two anodes 180 degrees around the axis.

8. The stereo x-ray generating device according to claim 1, in which the tip of the anode has an inclined surface.

9. The stereo x-ray generating device according to claim 8, in which:
   a magnetic body is attached to the opposite side of each tip of the anode, and
   the movement to and fro of each anode along the axis of the chamber is performed by electrification to the electromagnet or solenoid provided at the end of the chamber.

10. The stereo x-ray generating device according to claim 8, in which:
    a magnetic body is attached to the opposite side of each tip of the anode, and
    the movement to and fro of each anode along the axis of the chamber is performed by electrification to the electromagnet or solenoid provided at the end of the chamber,
    the inclined surface consists of two inclined surfaces, these two inclined surfaces are provided together on either side of the axis,
    the angle of inclination of the two inclined surfaces are the same, the axial positions of the two inclined surfaces are different,
    the anode and the cathode are moved closer or apart by turning the two anodes 180 degrees around the axis.

\* \* \* \* \*